(12) United States Patent
Hess et al.

(10) Patent No.: US 7,281,314 B2
(45) Date of Patent: Oct. 16, 2007

(54) METHOD FOR IMPLEMENTING AN ANTENNA SYSTEM

(75) Inventors: Philip B. Hess, Los Angeles, CA (US); Wayne A. Morgan, Northridge, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 11/447,564

(22) Filed: Jun. 5, 2006

(65) Prior Publication Data

US 2006/0227060 A1    Oct. 12, 2006

Related U.S. Application Data

(62) Division of application No. 10/692,541, filed on Oct. 24, 2003, now Pat. No. 7,123,206.

(51) Int. Cl.
*H01P 11/00* (2006.01)
(52) U.S. Cl. .......................... 29/600; 343/788; 343/787
(58) Field of Classification Search ....... 29/600–602.1, 29/830–831, 832–834; 343/741–742, 787–788, 343/766–767
See application file for complete search history.

(56) References Cited

U.S. PATENT DOCUMENTS

| 2,354,332 | A | * | 7/1944 | Polydoroff | ................... 343/788 |
| 4,210,859 | A |   | 7/1980 | Meretsky et al. | |
| 6,396,455 | B1 | * | 5/2002 | Ely et al. | ..................... 343/788 |
| 6,538,616 | B1 |   | 3/2003 | Bedard | |
| 6,577,284 | B1 | * | 6/2003 | Conti | .......................... 343/788 |
| 7,123,206 | B2 | * | 10/2006 | Hess et al. | .................. 343/788 |
| 2002/0080083 | A1 |   | 6/2002 | Nantz et al. | |

FOREIGN PATENT DOCUMENTS

DE       19533105 A1    9/1995
WO    WO 03/075403 A1   9/2003

OTHER PUBLICATIONS

PCT International Search Report as issued in International Application No. PCT/US04/032688, Mailing date Dec. 30, 2004.

* cited by examiner

*Primary Examiner*—Minh Trinh
(74) *Attorney, Agent, or Firm*—Foley & Lardner LLP

(57) ABSTRACT

A system and method for implementing an antenna system for multiple antennas using a single core. The method may include providing a first core, a first winding would about the first core for transmitting/receiving electromagnetic signals, and a second winding for transmitting/receiving electromagnetic signals would about the first core and the first winding. The first winding and the second winding may be wound such that a direction of a first magnetic field generated by the first winding is different than a direction of a second magnetic field generated by the second winding. The method may also include proving for activation circuitry connected to the first winding and the second winding. The activation circuitry may activate the first winding separately from the second winding. The method may provide three or more coils/antennas disposed on a single core. The method may choose stronger of the received magnetic fields from the first or the second coil, for processing.

24 Claims, 7 Drawing Sheets

METHOD FOR IMPLEMENTING AN ANTENNA SYSTEM

CROSS-REFERENCE TO RELATED PATENT APPLICATIONS

This application is a Divisional of U.S. application Ser. No. 10/692,541 filed Oct. 24, 2003, now U.S. Pat. No. 7,123,206, issued Oct. 27, 2006, incorporated herein by reference in its entirety.

BACKGROUND

1. Field of the Invention

The present invention relates to systems and methods for providing a plurality of antennas using a single core and, in particular embodiments, to systems and methods for providing an implantable device having multiple antennas and a single core that is inductively coupled to an external unit.

2. Description of Related Art

The ability to inductively couple radio signals between two or more coils has greatly facilitated the use of implantable devices in patients who require internal monitoring, sensing or regulation of various physical parameters or who require internal delivery of a drug or medication. RF communication between an implant unit and an external device has allowed many such patients to receive effective medical treatment and/or analysis while maintaining mobility realizing the mobility and other benefits of an implanted device.

For example, for patients requiring automatic pacing of the heart, implantable pacing devices can record electrical activity in the heart and the response of the heart to pacing signals. The recorded information can then be transmitted via inductive coupling of RF signals to a receiving unit external to the patient and be analyzed and evaluated by an attending physician. The ability to inductively couple data via RF transmission eliminates the need for costly and burdensome invasive surgery to recover recorded data in the implant unit.

In a similar manner, many diabetic patients utilize implantable pumps and insulin delivery systems for the regulated delivery of insulin to their bodies. These patients can also transmit recorded data relating to the delivery of insulin and the corresponding response by the body to an external unit where the data can be analyzed. In response to the analysis, the parameters of the insulin delivery system may be adjusted by inductive coupling of an RF signal from an external unit to the implant unit. No invasive surgery to reach the implant unit is necessary.

Inductively coupled implant units to date, however, have not given patients complete freedom from external monitoring or control devices. The quasi-static magnetic filed produced by a coil is highly directional in nature and the link between a coil in an implant unit and a coil in an external unit depends on the relative orientation between transmitter and receiver coil antennas. To ensure a reliable link independent of transmitter and receiver orientation, the ability to generate or receive a modulated magnetic field in more than one direction is required, which, in turn, requires the use of multiple antenna coils.

In past designs having multi-directional magnetic field performance, separate antennas, each having its own air or ferrite core, have been used for multi-directional magnetic field transmission and reception. A design of this type may be seen in FIG. 1. In FIG. 1, an implantable circuit 10 includes having integrated circuits 18 includes three separate antennas 12, 14 and 16, one for each axis in three-dimensional space and each antenna having its own core. For effective multi-directional operation, at least one of the antennas 12, 14 and 16 must be oriented in a plane perpendicular to two of the antennas, as shown in FIG. 1. This type of configuration greatly increases the space required to house the system. Since space in an implantable unit is critical and always at a premium, the space required by this type of three-antenna system is relatively large and, thus, is a drawback for patients who are outfitted with an implant unit utilizing this type of system.

Because of the space issues associated with a design of the type shown in FIG. 1, other past designs have incorporated only a single antenna for data transmission/reception. Single antenna designs generate a highly directional magnetic field. For operation, a patient having a single antenna implant device has had to position an external unit directly adjacent to the implant device and in align the antenna of the external device with the antenna of the implant unit to effect transmission or reception. Systems of this type have mobility limitations, rendering the patient stationary while trying to transmit or receive data. In addition, because of the directional nature of the a single antenna device, and the inability of the patient to ascertain the exact orientation of the implanted antenna, maximum data transfer rates and accuracy may be diminished in a single antenna system.

SUMMARY

It is therefore an object of embodiments of the present invention to provide systems and methods for multiple antennas that utilize a single core. It is a further object of embodiments of the present invention to provide an inductively coupled system that can transmit and receive signals in three dimensions. It is yet a further object of embodiments of the present invention to provide a method of making and using a multiple antenna system that utilizes a single core.

An antenna system according to an embodiment of the present invention may include a first core; a first winding disposed about the first core for transmitting/receiving electromagnetic signals; a second winding for transmitting/receiving electromagnetic signals disposed about the first core and the first winding; and activation circuitry connected to the first winding and the second winding. The first winding and the second winding may be wound such that a direction of a first magnetic field generated by the first winding may be different than a direction of a second magnetic field generated by the second winding. The activation circuitry may activate the first winding separately from the second winding.

The first core may be air or a ferrite. The first winding may be wound as a helical solenoid or a rectangular solenoid around the first core. The second winding may also be wound as a helical solenoid a rectangular solenoid around the first core.

Embodiments of the present invention may also include a third winding disposed about the first core, the first winding and the second winding. The third winding may be wound such that a direction of a third magnetic field generated by the third winding may be different than the direction of the first magnetic field and the second magnetic field. The third winding may be wound as a helical solenoid or a rectangular solenoid around the first core.

The activation circuitry may include a multiplexer for facilitating separate activation of the first winding, the second winding or the third winding. The first winding, the second winding and the third winding may transmit or receive a radio frequency signal. The direction of the first magnetic field may be orthogonal to the direction of the second magnetic field and the direction of the third magnetic field may be orthogonal to the direction of the first magnetic field and the second magnetic field.

Embodiments of the present invention may also include a second core; a fourth winding disposed about the second core for transmitting/receiving electromagnetic signals; and a fifth winding for transmitting/receiving electromagnetic signals disposed about the second core and the fourth winding. The fifth winding may be serially connected to the second winding.

According to an embodiment of the present invention, an inductively coupled system may include a first core disposed on an implantable unit; a local first winding disposed about the first core for transmitting/receiving RF signals; at least one local second winding for transmitting/receiving electromagnetic signals disposed about the first core and the local first winding; a second core disposed on a remote unit; a remote first winding disposed about the second core for transmitting/receiving RF signals; and at least one remote second winding for transmitting/receiving electromagnetic signals disposed about the second core and the remote first winding. Magnetic fields may be coupled between the local first winding and the at least one local second winding on the first core; and the remote first winding and the at least one remote second winding on the second core.

The at least one local second winding may include one winding or two windings. The at least one remote second winding may include one winding or two windings. The implantable unit may be disposed internally in a body. Thee remote unit may be disposed internally to a body or externally to a body.

A method for implementing an antenna system may include providing a core; winding a first coil for transmitting/receiving electromagnetic signals about the core; winding a second coil for transmitting/receiving electromagnetic signals about the first core and the first winding; and activating the first coil separately from the second coil. The core provided may be an air core or a ferrite core.

The first coil and the second coil may be wound as a helical solenoid or a rectangular solenoid around the core. The system may also include a third coil for transmitting/receiving electromagnetic signals about the core, the first winding and the second winding. The third coil may be wound as a helical solenoid or a rectangular solenoid around the core. The first coil, the second coil and the third coil may be wound orthogonal to each other.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Although the following description is directed primarily toward methods and systems for inductively coupling an implant unit to an external device via multiple antennas having a single core, embodiments of the present invention may be used in a variety of capacities and applications. For example, embodiments of the present invention may be used to couple one external device to another external device or to couple one internal device to another internal device. Generally, embodiments of the present invention may be adapted for use in any type of system where RF communication between two or more units is desired.

In addition, embodiments of the present invention may be used in a variety of applications. For example, embodiments of the present invention may be used with implantable pumps that deliver insulin to diabetics and external control units used in connection with the implantable pumps. Also, embodiments of the present invention may be used in pacemaker and defibrillator systems and external control units or analysis units used in connection therewith.

Figure 1:
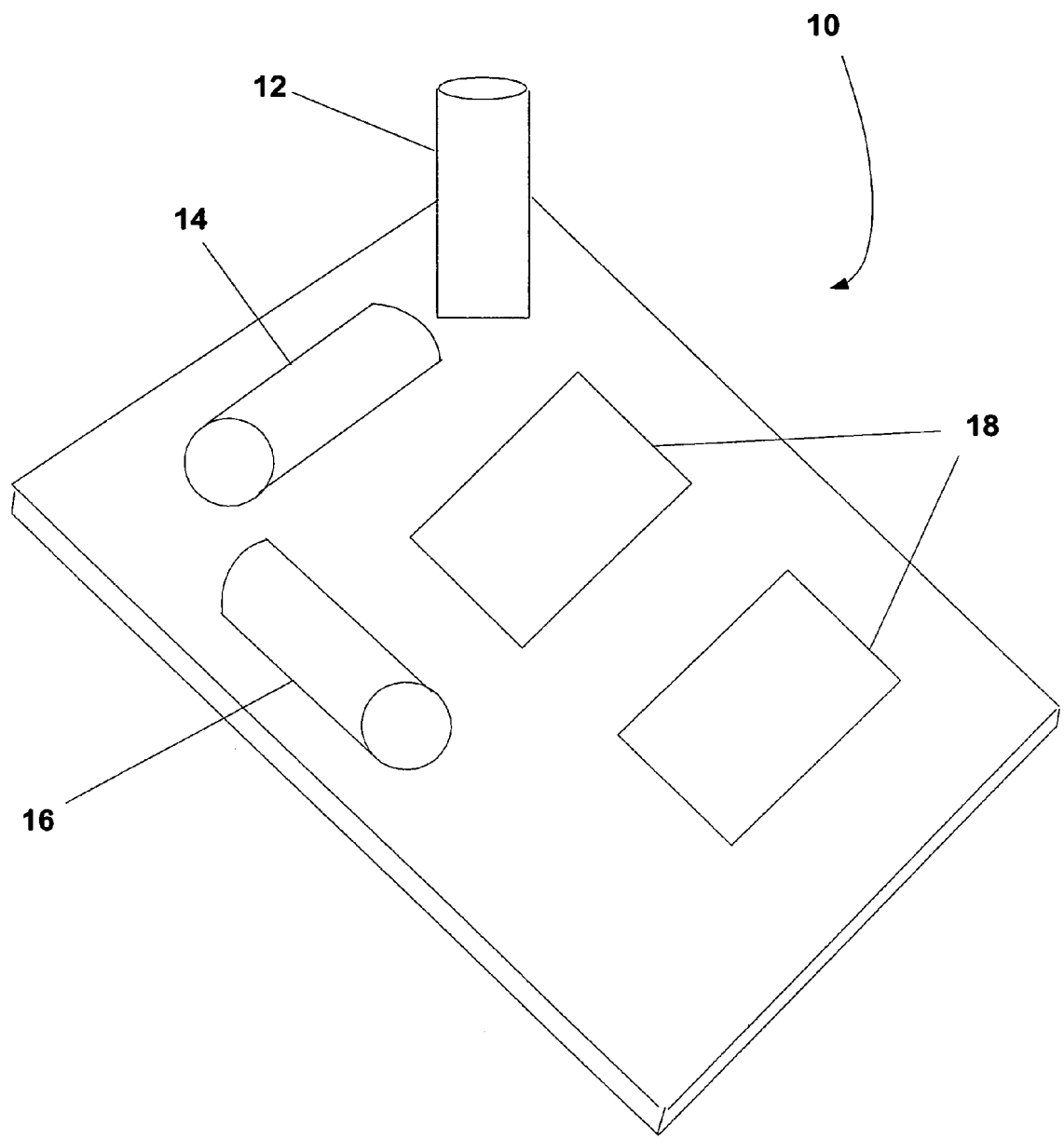
FIG. 1 shows a conventional three-antenna system according to the prior art.
Figure 2:
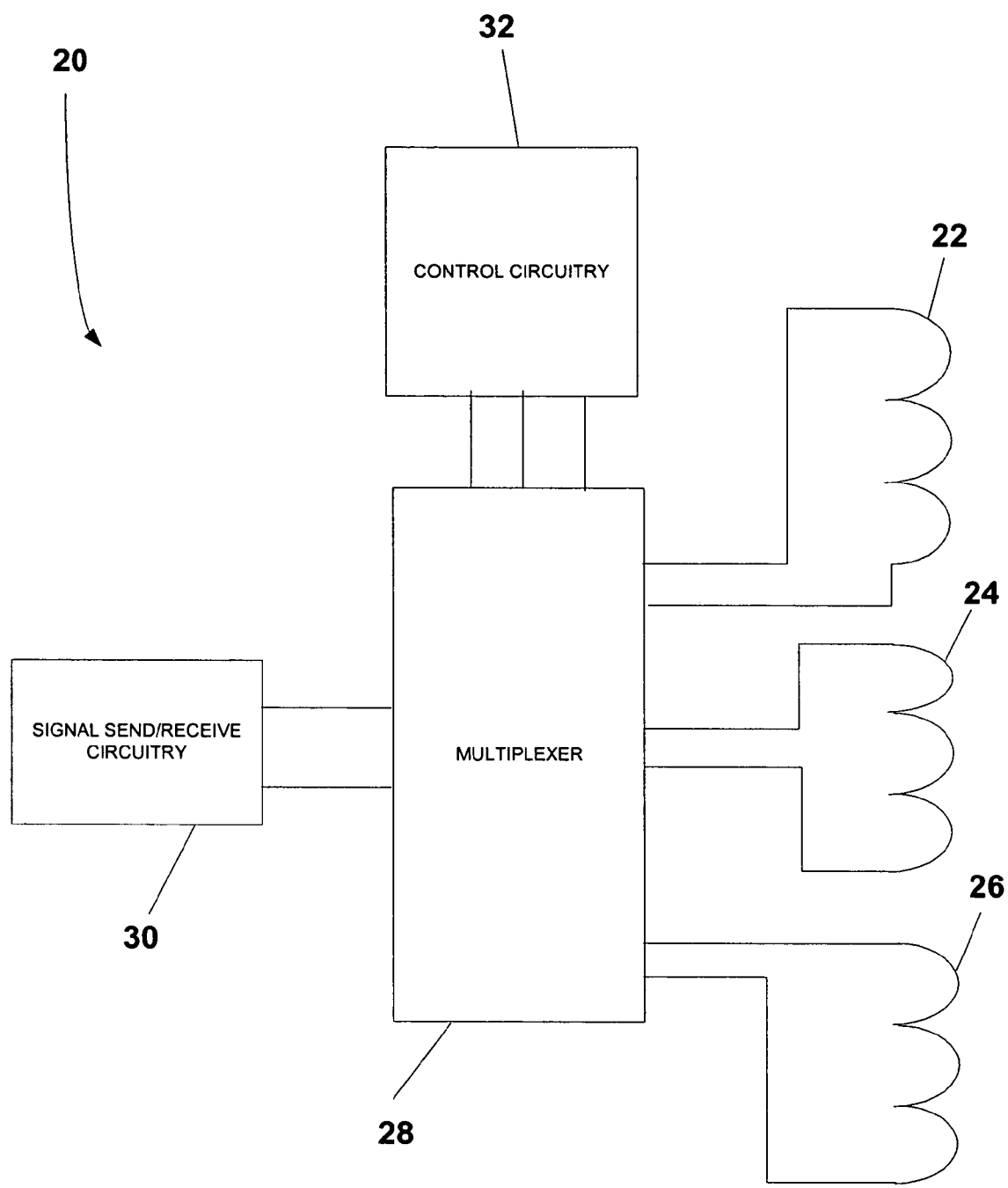
FIG. 2 is a generalized block diagram of a system having multiple antennas utilizing a single core according to an embodiment of the present invention.

A generalized block diagram of a multiple antenna system 20 utilizing a single core according to an embodiment of the present invention is shown in FIG. 2. The multiple antenna system 20 includes, without limitation, a first antenna 22, a second antenna 24, a third antenna 26, a multiplexer 28, control circuitry 32 and RF signal send/receive circuitry 30. According to embodiments of the present invention, two of the three antennas 22, 24 and 26 or all three of the antennas 22, 24 and 26 may be disposed about a single core, as will be described in greater detail below.

According to an embodiment of the present invention, the multiplexer 28 may be controlled by the control circuitry 32 to connect the RF signal send/receive circuitry 30 to only one of the first antenna 22, second antenna 24 and third antenna 26 at a time. In other words, the first antenna 22, second antenna 24 and third antenna 26 may be time-multiplexed so that only one antenna is active to send or receive RF signals or other magnetic or electromagnetic signals to a remote unit by activating only one antenna at a time, interference from another antenna in the system is eliminated. The multiplexer 28 itself may be implemented with a commercially available multiplexer integrated circuit, or may be implemented with discrete components, or may be part of an application specific integrated circuit (ASIC), Other implementations common in the art may also be used.

The control circuitry 32 may be used to configure a channel on the multiplexer 28. The control circuitry 32 may also be implemented in a variety of ways. The control circuitry 32 may be a discrete microprocessor or may be discrete components in a state machine. According to another embodiment of the present invention, the control circuitry 32 may be part of the same ASIC that includes the multiplexer 28, if such a configuration is used.

According to the embodiment of the invention shown in FIG. 2, the RF signal send/receive circuitry 30 may be routed via the multiplexer 28 to the first antenna 22, the second antenna 24 or the third antenna 26 depending on the channel of the multiplexer 28 selected by the control circuitry 32. The RF signals may be generated and the RF signal send/receive circuitry 30 may be implemented according to standard techniques common in the art.

Also, multiple send/receive circuits may be used. According to an embodiment of the present invention, two, three or more send/receive circuits may be incorporated into the multiple antenna system 20. For example, if three send/receive circuits were to be incorporated into the multiple antenna system 20, each of the three send/receive circuits could be logic controlled. Accordingly, there could also be three transmitters/receivers which could be operating simultaneously. Thus, signals could be received on each of the three receivers and processed separately. The strongest or otherwise most desirable signal could then be chosen from the three. According to embodiments of the present invention, schemes of this type may be advantageous in that a transmitting device may need to send a signal only once, as opposed to multiple times, to ensure adequate receipt of the signal. Also, simultaneous signal transmission would be possible.

Figure 3:
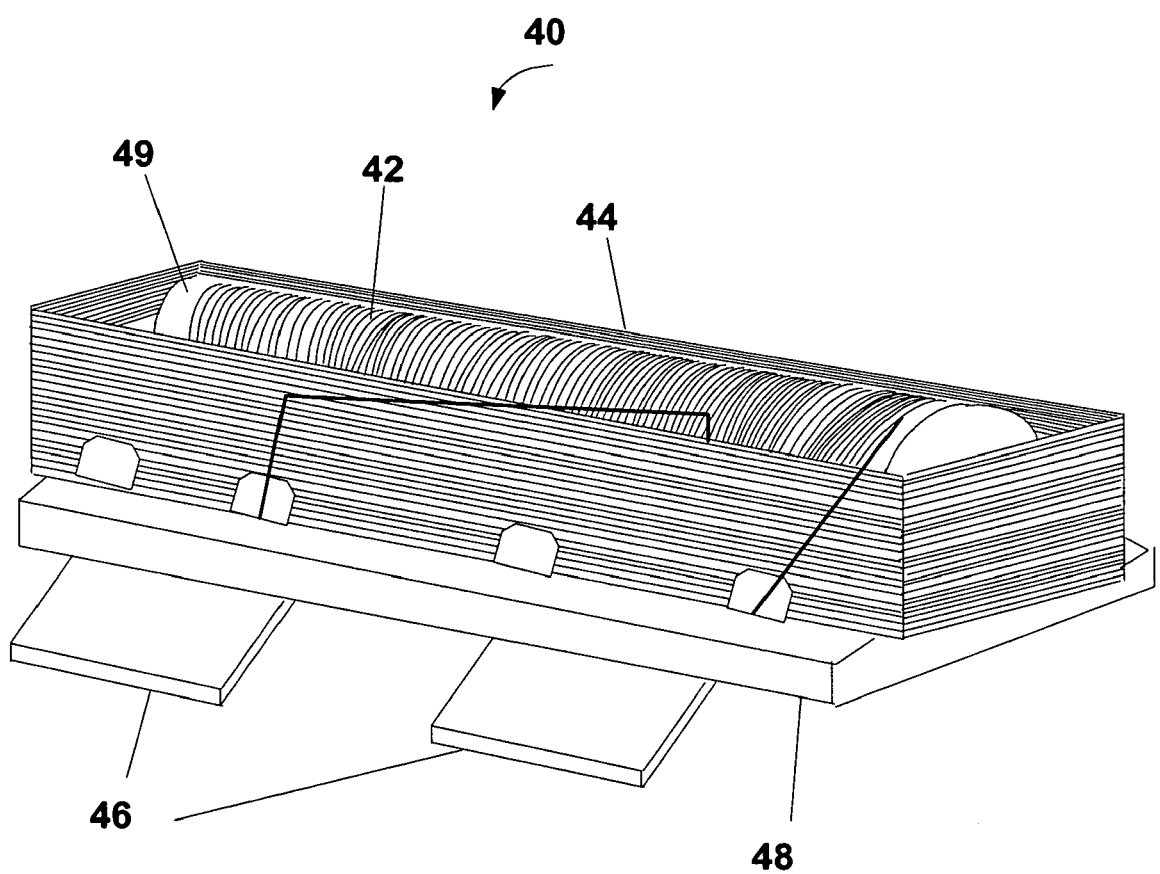
FIG. 3 is a perspective view of a generalized scheme for winding two antennas on a single core according to an embodiment of the present invention.

A generalized scheme implementing a two antenna system 40 on a single core according to an embodiment of the present invention is shown in FIG. 3. The embodiment shown in FIG. 3 includes, without limitation, a core 49, a first coil 42, and a second coil 44. The core 49 may be a ferrite rod or block or other material having high magnetic permeability. According to another embodiment of the present invention, the core 49 may be an air core.

The core 49 may be of a standard cylindrical or rectangular shape as is common in the art. According to an embodiment of the present invention, a rectangular core may have dimensions of approximately 5 mm×20 mm. However, the dimensions of the core 49, whether oval, rectangular or some other geometry, may vary according to the application and the space constraints of application for which embodiments of the present invention is desired.

The first coil 42 may be cylindrically or helically wrapped around the core 49 and forms a first antenna. The second coil 44 may be wound transversely around the ends of the core 49, in the shape of a rectangle or an oval, for example, and forms a second antenna. Thus, both the first coil 42 and the second coil 44 may be wound around the same core 49. Each coil, therefore, utilizes a single core and the additional space requirements of a separate core for each antenna are eliminated. If the first coil 42 and the second coil 44 are fabricated such that the windings of each coil are orthogonal to each other, magnetic fields generated in each coil will also be orthogonal to each other. In such a scheme, transmission/reception may be effected completely in two dimensions.

The core 49, the first coil 42 and the second coil 44 may sit on a generic housing 48. The second coil 44, which, according to the embodiment of the invention shown in FIG. 3 is wound transversely around the end of the core 49, may be self-supporting. However, the housing 48 may be designed such that the second coil 44 need not be self-supporting. The embodiment of the invention shown in FIG. 3 may also include connection pads 46 (two for each coil in the embodiment shown) for providing connection points to the coils.

Figure 4:
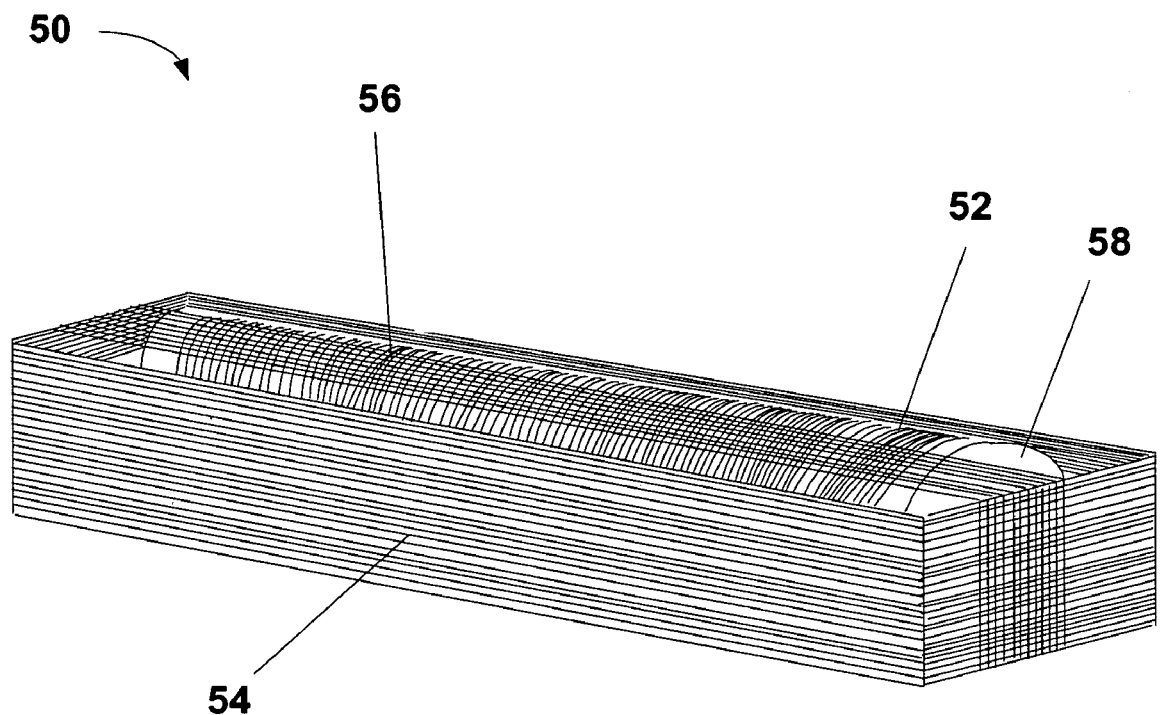
FIG. 4 is a perspective view of a generalized scheme for winding three antennas on a single core according to an embodiment of the present invention.

A generalized scheme implementing a three antenna system 50 on a single core according to an embodiment of the present invention is shown in FIG. 4. The embodiment of the invention shown in FIG. 4 is similar to that shown in FIG. 3, having a core 58, a first coil 52 cylindrically wrapped about the core 58, and a second coil 54 wrapped transversely about the ends of the core 58. In addition, the embodiment of the invention shown in FIG. 4 includes, without limitation, a third coil 56 wrapped transversely to the first coil 52 and the second coil 54. The first coil 52, second coil 54 and third coil 56 may all be wound orthogonal to each other such that magnetic fields generated in each coil are also orthogonal to each other. Thus, the antenna system 50 shown in FIG. 4 provides transmission/reception in three dimensions.

In operation, the embodiment of the inventions shown in FIG. 3 and FIG. 4 may transmit or receive RF signals or other magnetic or electromagnetic signals in two dimensions and three dimensions, respectively. Embodiments of the invention may be expanded such that a plurality of more than three coils are wound about a single core. While some of the coils may be wound orthogonal to one another, other coils may be wound at various angles with respect to the core axes to provide enhanced transmission or reception in each dimension.

Figure 5:
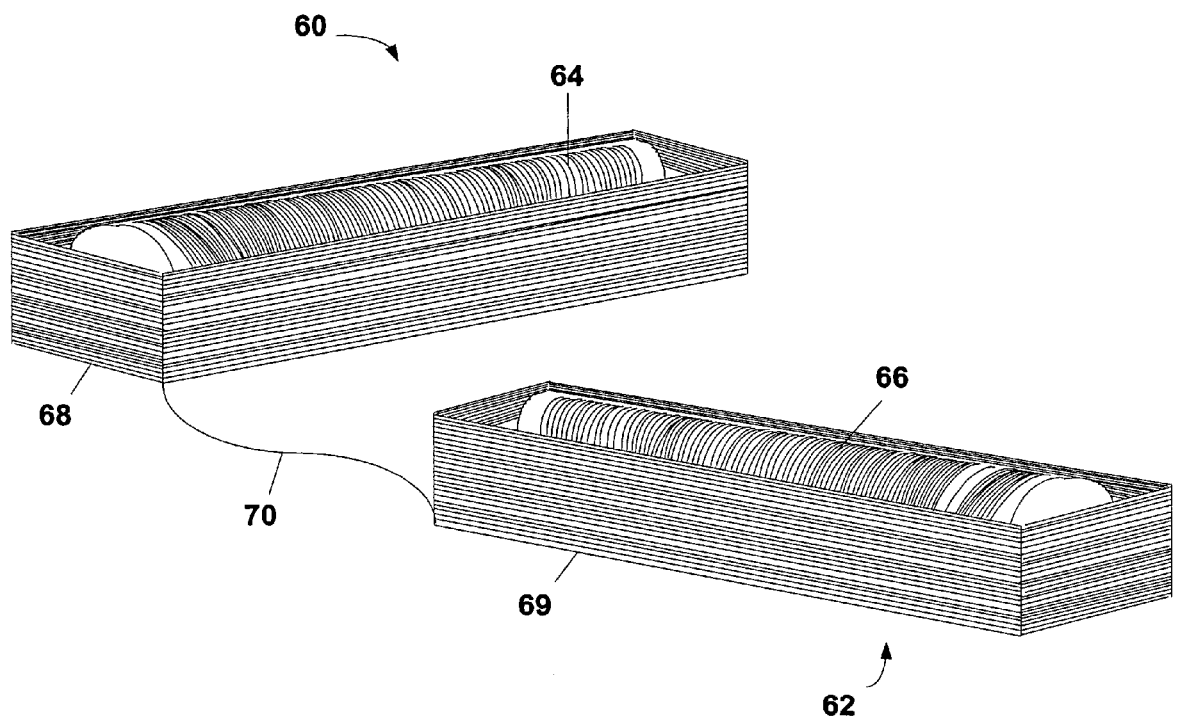
FIG. 5 is a perspective view of a generalized scheme for connecting antennas in series according to an embodiment of the present invention.

A generalized scheme showing a serial connection of a first antenna system 60 with a second antenna system 62 according to an embodiment of the present invention is shown in FIG. 5. The first antenna system 60 and the second antenna system 62 are each similar to the antenna system 40 shown in FIG. 3. The first antenna system 60 includes, without limitation, a core 72, a first coil 64, and a second coil 68. Likewise, the second antenna system 62 includes, without limitation, a core 74, a first coil 66, and a second coil 70.

Each of the cores 72 and 74 may be a ferrite rod or block or other material having high magnetic permeability. According to another embodiment of the present invention, each of the cores 72 and 74 may be an air core. Each of the cores 72 and 74 may be formed into a variety of geometries, such as a cylinder or a rectangle, for example.

Each of the first coils 64 and 66 may be cylindrically or helically wrapped around the cores 72 and 74, respectively, to form antennas. Each of the second coils 68 and 70 may be wound transversely around the ends of cores 72 and 74, respectively, in the shape of a rectangle or an oval, for example, also forming antennas.

According to the embodiment of the invention shown in FIG. 5, the first antenna system 60 may be positioned at a right angle to the second antenna system 62. Thus, if the windings of the first coils 64 and 66 are in the same direction, because the first coils 64 and 66 are at right angles to one another, each of the first coils 64 and 66 form an orthogonal antenna system, permitting the transmission and/or reception of magnetic fields or other RF fields in two dimensions. However, if the second coils 68 and 70 are wound in the same direction, the positioning of the first antenna system 60 to the second antenna system 62 dictates that the second coils 68 and 70 will generate magnetic fields in the same direction. Thus, the magnetic fields of each of the second coils 68 and 70 may be enhanced by a serial connection 76, thereby increasing the effective area of the second coils 68 and 70 and producing a larger magnetic field since the strength of the magnetic filed produced or received is proportional to the antenna aperture area.

Moreover, because of the right angle positioning of the first antenna system 60 and the second antenna system 62, the second coils 68 and 70 will generate magnetic fields in a direction orthogonal to the magnetic fields generated by the first coils 64 and 66. Accordingly, the embodiment of the invention shown in FIG. 5 forms a three-dimensional transmission/reception system. The embodiment of the invention shown in FIG. 5 may be desirable for three-dimensional transmission/reception applications in which the winding of a third antenna around a single core is not feasible or is impractical but space is available for a second core.

Figure 6:
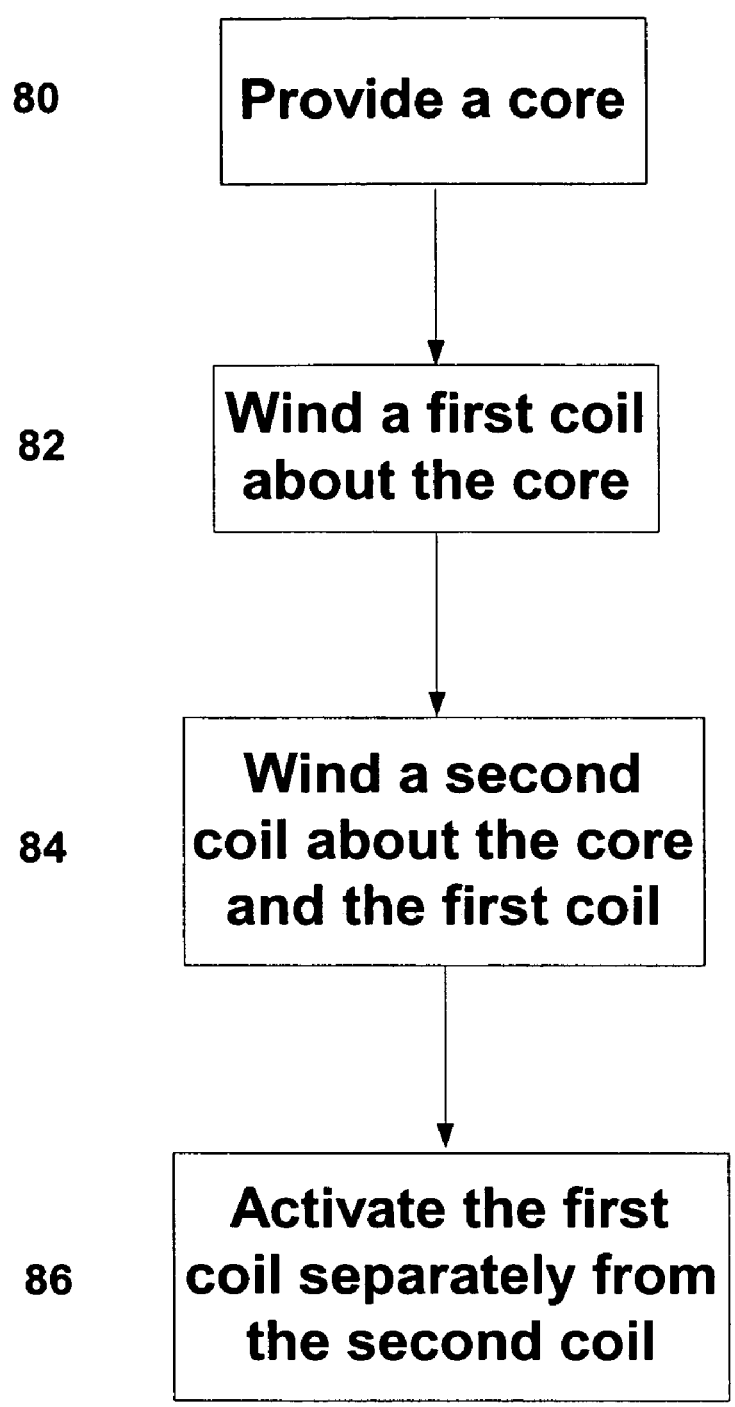
FIG. 6 is a flow chart of a generalized method for implementing an antenna system according to an embodiment of the present invention.

A generalized method for implementing an antenna system according to an embodiment of the present invention is shown in FIG. 6. At step 80, a core is provided. The core may be an air core or a ferrite core and may be cylindrical or rectangular in shape.

At step 82, a first coil is wound about the core, forming a first antenna. The first coil may be wound in a cylindrical or helical fashion. At step 84, a second coil is wound about the core and the first coil, forming a second antenna. The second coil may be wound in a rectangular or oval fashion.

At step 86, the first coil and the second coil are activated for transmission or reception separately from one another. Thus, only the first coil or the second coil will be active for transmitting or receiving signals. The first coil and the second coil may be activated by multiplexer circuitry or other switching circuitry.

The method shown in FIG. 6 may be expanded to more than two coils. For example, if an embodiment of the invention of the type shown in FIG. 4 were implemented in application, i.e., an antenna system having three coils on a single core, the method shown in FIG. 6 could be expanded to a three coil/antenna system. Thus, for example, the method could include, without limitation, providing a single core; winding a first coil about the core; winding a second coil about the core and the first coil; winding a third coil about the core, the first coil and the second coil; and activating the first, second and third coils separately during the transmission and reception of RF signals with a remote unit.

Figure 7:
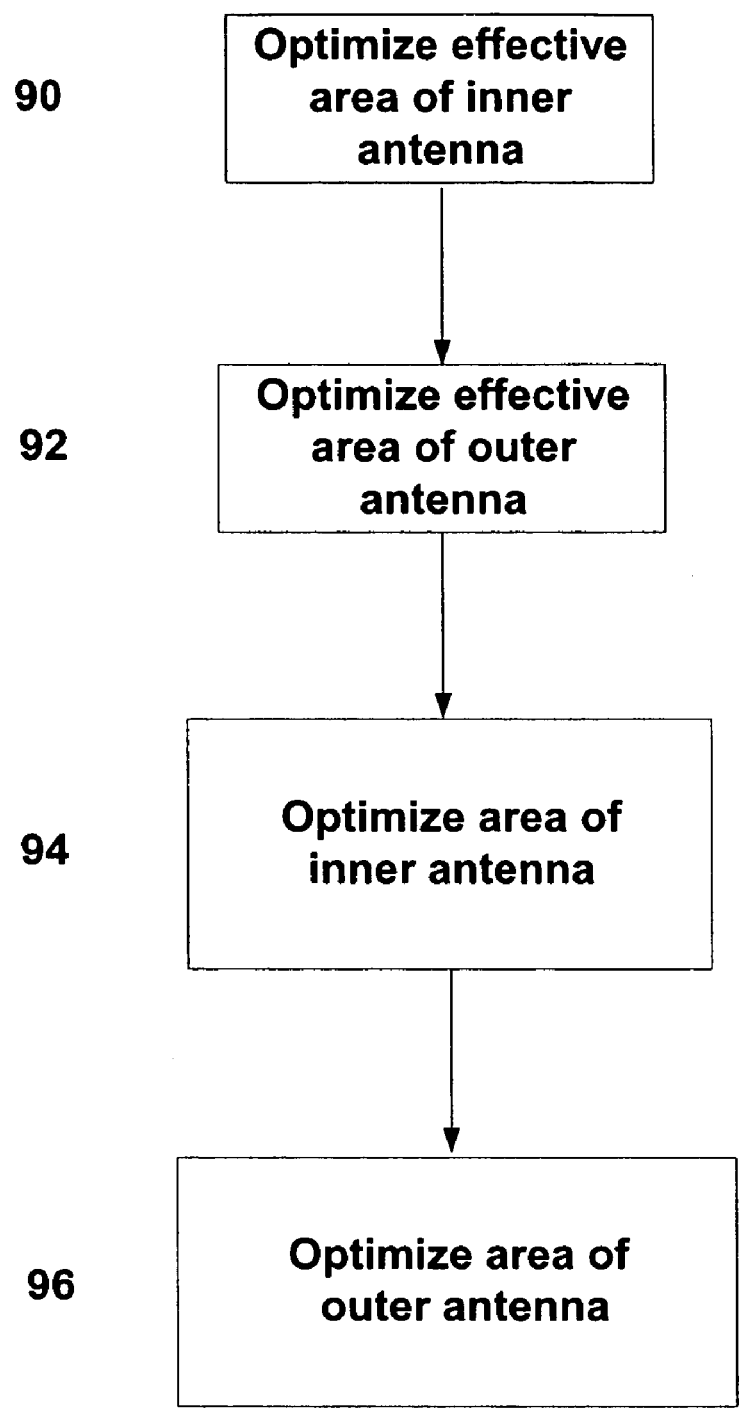
FIG. 7 is a flow chart of a generalized method for optimizing an antenna system according to an embodiment of the present invention.

A generalized scheme for optimizing antenna parameters is shown in FIG. 7. It is possible and may be desirable to optimize certain parameters for two or more antennas. For example, for embodiments of the invention having one or more inner cylindrical coils and one or more outer rectangular coils, it may be desirable to optimize the dimensions of the inner antenna (or antennas) for a very high effective permeability of the inner core ($\mu_{inner\ core}$) and, thus, the effective area of the inner antenna or antennas. At the same time, it may be desirable to optimize the dimensions of the outer antenna (or antennas) to increase the effective area of the outer antenna or antennas. However, such parameters are not necessarily mutually exclusive and, thus, a balancing between optimizations may be desired. Although the scheme in FIG. 7 shows consecutively progressing steps, the steps may be performed in any order or may be performed simultaneously with one another.

At step 90, the effective area of the inner antenna may be optimized. The effective area of the coil is equal to the effective permeability of the core times its area, i.e., $$\text{Area}_{eff} = \mu_{eff} \times \text{Area} \quad [1]$$

The effective area of the inner antenna may be optimized according to the following equation:

$$\mu_{inner\ core} \propto \text{length}_{inner\ core}/\text{diameter}_{inner\ core} \quad [2]$$

According to equation [2], the larger the length/diameter of the inner core, rod or block, the greater the effective permeability of the inner core and, thus, the greater the effective area of the inner antenna.

At step 92, the effective area of the outer antenna may be optimized. The effective area of the outer antenna may be optimized according to the following equation:

$$\mu_{rectangle} \propto \text{height}_{rectangle}/(\text{length}_{rectangle} \times \text{width})_{rectangle} \quad [3]$$

According to equation [3], the larger the height/(length×width) of the outer rectangle, the greater the effective permeability of the outer core and, thus, the greater the effective area of the outer antenna.

At step 94, the area of the inner antenna is optimized, taking into account that the larger the diameter of the inner antenna, the larger the area of the inner antenna. At step 96, the area of the outer antenna is optimized, taking into account that the larger the product of the length and the width of the outer antenna, the larger the area of the outer antenna.

It is important to consider optimizing both the actual area and the effective area of the inner and outer antennas because the larger the area, the larger the transmitted or received field strength while the larger the effective area, the larger the transmitted or received voltage. However, as can be seen by comparing equations [2] and [3], increasing the length of the inner coil and, accordingly, the effective area of the inner antenna, the effective permeability of the outer rectangle is simultaneously reduced. Thus, although some of the parameters associated with the inner and outer antennas may be opposed, they may still be individually or concurrently optimized for the characteristics of a desired application.

In addition, according to embodiments of the present invention, the antennas may be shielded. For example, the antennas may be shielded by surrounding the antennas with a grounded metal. Any of a variety of metals may be used, such as copper or aluminum, for example. In addition, the metal used may be a solid piece of metal or may be a metal mesh. The actual geometry of the shield by vary and may be determined by any number of techniques that are common in the art. The optimum geometry of the shield may depend on a variety of factors, including, without limitation, the number of coils and the position of each of the coils with respect to each other. In some circumstances, the geometry of the shield may be determined simply by trial and error.

Also, the coils, instead of or in addition to being shielded, may also be electrically balanced. Both balancing and shielding reduces the effect of electrostatic noise in a transmitted or received signal, thereby increasing the overall reliability of the system.

Embodiments of the present invention may be used in a variety of applications. For example, embodiments of the present invention may be used in connection with implantable insulin pumping mechanisms with associated external controller/communication units. Mechanisms of this type may be used by diabetics in lieu of routine glucose level testing and insulin injection. When operating embodiments of the invention for this particular application, a diabetic patient may require that data relating to glucose monitoring and insulin delivery be transmitted to a remote controller/communication unit. Thus, if the patient were outfitted with an embodiment of the present invention having three coils/antennas, thereby permitting transmission in three dimensions, the patient need simply to position herself within the operating range of system in order to transmit data. Because the implant unit is capable of transmitting data in three dimensions, there is no need for the patient to align herself with the remote controller/communication unit. Data will be transmitted along all three coordinate axes and received by the remote controller/communication unit. This offers a tremendous advantage in ease of use for the patient.

Likewise, once data is received by the remote controller/communication unit, the remote controller/communication unit may determine that adjustments to the implant unit are necessary, such as, for example, an increase/decrease in the frequency of glucose sample points, an increase/decrease in the amount of insulin delivered to the patient, and the like. Thus, data must be transmitted from the remote controller/communication unit and received by the implant unit.

Reception of the data by the implant unit from the remote controller/communication unit is accomplished in a manner similar to the transmission of data from the implant unit to the remote controller/communication unit. If the three coil/antenna system has been implemented, the patient need only position herself within the operating range of the system. Because the three coils of the implant unit receive data in three dimensions, data transmitted by the remote controller/communication unit will be detected by the implant unit regardless of the orientation of the implant unit with respect to the remote controller/communication unit.

Embodiments of the present invention may transmit and/or receive signals at a variety of frequencies and power levels. The frequencies and power levels implemented in embodiments of the present invention will depend on the application, the needs of the system, and the needs of the user. According to an embodiment of the present invention, RF signal transmission/reception may occur at 30 MHz or less. Other embodiments of the present invention may transmit/receive at frequencies greater than 30 MHz.

Also, according to embodiments of the present invention, signal transmission/reception may be effective up to approximately 3 feet. Power levels that transmit/receive at distances greater than 3 feet may be implemented depending on the needs dictated by the system and the patient.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A method for implementing an antenna system comprising:
   providing a core;
   winding a first coil for transmitting/receiving electromagnetic signals about the core;
   winding a second coil for transmitting/receiving electromagnetic signals about the core and the first coil;
   activating the first coil separately from the second coil;
   receiving a magnetic field with the first coil, the magnetic field relating to information transmitted by a source;
   receiving the magnetic field with the second coil, the magnetic field relating to the same information transmitted by the source,
   activating both the first coil and the second coil to receive the magnetic field including;
   choosing a stronger of the received magnetic field at the first coil and the received magnetic signal at the second coil for processing; and,
   processing signals corresponding to the chosen received magnetic fields.

2. The method of claim 1, wherein the core provided is an air core.

3. The method of claim 1, wherein the core provided is a ferrite core.

4. The method of claim 1, wherein the first coil is wound as a helical solenoid around the core.

5. The method of claim 1, wherein the first coil is wound as a rectangular solenoid around the core.

6. The method of claim 1, wherein the second coil is wound as a helical solenoid around the core.

7. The method of claim 1, wherein the second coil is wound as a rectangular solenoid around the core.

8. The method of claim 1, further comprising winding a third coil for transmitting/receiving electromagnetic signals about the core, the first coil and the second coil.

9. The method of claim 8, wherein the third coil is wound as a helical solenoid around the core.

10. The method of claim 8, wherein the third coil is wound as a rectangular solenoid around the core.

11. The method of claim 8, wherein the first coil, the second coil and the third coil are wound orthogonal to each other.

12. The method of claim 1, wherein the first coil and the second coil are wound orthogonal to each other.

13. The method of claim 1, further comprising:
   generating a first magnetic field with the first coil in response to a data signal; and
   generating a second magnetic field with the second coil in response to the same data signal.

14. The method of claim 13, further comprising sending the data signal to the first coil and to the second coil simultaneously.

15. The method of claim 13, further comprising sending the data signal to the first coil at a first time and to the second coil at a second time different from the first time.

16. The method of claim 1, further comprising activating only one of the first coil and the second coil at a time to receive the magnetic field.

17. The method of claim 1, further comprising disposing the core on an implantable unit configured for implantation in a body of a medical patient.

18. A method for implementing an antenna system comprising: providing a core;
   winding a first coil for transmitting/receiving electromagnetic signals about the core;
   winding a second coil for transmitting/receiving electromagnetic signals about the core and the first coil;
   activating both the first coil and the second coil to receive the magnetic field;
   receiving a magnetic field with the first coil;
   receiving the magnetic field with the second coil; and
   choosing a stronger of the received magnetic field at the first coil and the received magnetic signal at the second coil for processing; and
   processing signals corresponding to the chosen received magnetic fields.

19. The method of claim 18, further comprising winding a third coil for transmitting/receiving electromagnetic signals about the core, the first coil and the second coil.

20. The method of claim 18, wherein the first coil and the second coil are wound orthogonal to each other.

21. The method of claim 19, wherein the first coil, the second coil and the third coil are wound orthogonal to each other.

22. The method of claim 18, further comprising:
   generating a first magnetic field with the first coil in response to a data signal; and
   generating a second magnetic field with the second coil in response to the same data signal.

23. The method of claim 18, further comprising sending the data signal to the first coil and to the second coil simultaneously.

24. The method of claim 18, further comprising disposing the core on an implantable unit configured for implantation in a body of a medical patient.

* * * * *